(12) United States Patent
Baba et al.

(10) Patent No.: US 12,383,691 B2
(45) Date of Patent: Aug. 12, 2025

(54) GAS MEASUREMENT ADAPTER

(71) Applicant: NIHON KOHDEN CORPORATION, Tokyo (JP)

(72) Inventors: Yuya Baba, Tokorozawa (JP); Masayuki Inoue, Tokorozawa (JP); Fumihiko Takatori, Tokorozawa (JP); Takayuki Aoyagi, Tokorozawa (JP); Nobuhiko Makino, Kyoto (JP); Takahiro Nakajima, Kyoto (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 273 days.

(21) Appl. No.: 18/032,748

(22) PCT Filed: Dec. 17, 2021

(86) PCT No.: PCT/JP2021/046741
§ 371 (c)(1),
(2) Date: Apr. 19, 2023

(87) PCT Pub. No.: WO2022/145257
PCT Pub. Date: Jul. 7, 2022

(65) Prior Publication Data
US 2023/0321384 A1    Oct. 12, 2023

(30) Foreign Application Priority Data
Dec. 28, 2020    (JP) .................. 2020-219071

(51) Int. Cl.
G01N 21/05    (2006.01)
A61M 16/08    (2006.01)
(Continued)

(52) U.S. Cl.
CPC .......... *A61M 16/085* (2014.02); *G01N 21/05* (2013.01); *G01N 33/497* (2013.01); *A61M 2039/1077* (2013.01)

(58) Field of Classification Search
CPC ........ A61M 16/085; A61M 2039/1077; G01N 21/05; G01N 33/497; G01N 21/3504;
(Continued)

(56) References Cited

U.S. PATENT DOCUMENTS 5,910,287 A    6/1999    Cassin et al.
5,957,127 A    9/1999    Yamamori et al.
(Continued)

FOREIGN PATENT DOCUMENTS

JP    8-233699 A    9/1996
JP    2001-89526 A    4/2001
(Continued)

OTHER PUBLICATIONS

International Search Report (PCT/ISA/210) issued by the International Searching Authority on Apr. 7, 2022 in corresponding International Application No. PCT/JP2021/046741.
(Continued)

*Primary Examiner* — Kiho Kim
(74) *Attorney, Agent, or Firm* — Sughrue Mion, PLLC

(57) ABSTRACT

A gas measurement adapter includes a flow tube portion configured to allow gas to pass through the flow tube portion and a window portion configured to allow measurement light for measuring a component of the gas passing through the flow tube portion to pass through the window portion. The adapter is prepared by using an adapter forming material containing a cycloolefin-based resin as a main component.

9 Claims, 3 Drawing Sheets

(51) Int. Cl.
*G01N 33/497* (2006.01)
*A61M 39/10* (2006.01)

(58) Field of Classification Search
CPC .......... G01N 2021/8578; A61B 5/082; A61B 5/097; A61B 5/0873
See application file for complete search history.

(56) References Cited

U.S. PATENT DOCUMENTS

| | | | |
|---|---|---|---|
| 6,063,338 A | 5/2000 | Pham et al. | |
| 6,229,603 B1 | 5/2001 | Coassin et al. | |
| 6,232,114 B1 | 5/2001 | Coassin et al. | |
| 6,391,974 B1 | 5/2002 | Ogawa et al. | |
| 6,858,676 B1 | 2/2005 | Johoji et al. | |
| 9,702,805 B2 | 7/2017 | Takenaka et al. | |
| 2006/0132688 A1* | 6/2006 | Yoda | G02F 1/133634 349/119 |
| 2015/0377762 A1 | 12/2015 | Takenaka et al. | |
| 2016/0160373 A1 | 6/2016 | Hong et al. | |
| 2019/0105457 A1 | 4/2019 | Baba et al. | |

FOREIGN PATENT DOCUMENTS

| | | |
|---|---|---|
| JP | 2002-515125 A | 5/2002 |
| JP | 2019-18482 A | 2/2019 |
| JP | 2019-66436 A | 4/2019 |
| WO | 2014/118898 A1 | 8/2014 |

OTHER PUBLICATIONS

Written Opinion (PCT/ISA/237) issued by the International Searching Authority on Apr. 7, 2022 in corresponding International Application No. PCT/JP2021/046741.
Office Action issued on Jul. 30, 2024 by the Japanese Patent Office in corresponding JP Patent Application No. 2020-219071.
Office Action dated Dec. 3, 2024, issued by Japanese Patent Office in Japanese Patent Application No. 2020-219071.

* cited by examiner

GAS MEASUREMENT ADAPTER

CROSS REFERENCE TO RELATED APPLICATIONS

This application is a National Stage of International Application No. PCT/JP2021/046741 filed on Dec. 17, 2021, claiming priority from Japanese Patent Application No. 2020-219071 filed on Dec. 28, 2020, the disclosures of which are incorporated herein in their entirety by reference.

TECHNICAL FIELD

The presently disclosed subject matter relates to a sensor capable of detecting a predetermined respiratory gas (carbon dioxide, oxygen, laughing gas, volatile anesthesia gas, or the like) contained in respiratory gas of a living body, and a gas measurement adapter detachably attached to the sensor and having a passage through which a respiratory gas from the living body can pass.

BACKGROUND

In order to measure a specific component of a gas such as a respiratory gas, a gas measurement adapter including a transparent window is attached to a flow path of an artificial respirator that artificially performs respiration of a living body. Generally, such a gas measurement adapter has a configuration including a flow tube portion through which a gas passes and a window portion which transmits measurement light for measuring a component of the gas passing through the flow tube portion.

The gas measurement adapter is formed with the flow tube portion which is a passage through which the respiratory gas of a subject can pass. In the case of measuring a concentration of a predetermined respiratory gas (for example, carbon dioxide) contained in the respiratory gas of the subject, the window portion is disposed such that an optical axis connecting a light emitter and a light detector provided in a sensor crosses the passage. The measurement light (for example, infrared light) emitted from the light emitter is detected by the light detector, and a signal corresponding to the intensity of the detected light is output from the sensor (detection of carbon dioxide). The higher the concentration of carbon dioxide in the respiratory gas is, the stronger the measurement light (infrared light) is absorbed, and the weaker the intensity of detected light is. Therefore, the concentration of carbon dioxide contained in the respiratory gas of the subject can be measured by monitoring the intensity of the signal output from the sensor. An example of such a gas measurement adapter and sensor is disclosed in Patent Literature 1.

The gas measurement adapter (hereinafter, also referred to as an airway adaptor) in Patent Literature 1 is provided as a disposable airway case made of a hard resin.

CITATION LIST

Patent Literature

Patent Literature 1: JPH08-233699A

SUMMARY

Technical Problem

However, in the gas measurement adapter, at least the window portion through which the measurement light for measuring the component of the gas passes needs to allow the measurement light to pass through and be thin. That is, at present, the gas measurement adapter has a thin portion and is required to have excellent moldability having precision of detecting and emitting light, and there is room for further improvement in composition of a member thereof.

Therefore, an object of the presently disclosed subject matter is to provide a gas measurement adapter prepared by using a thin and moldable adapter forming material which transmits measurement light.

Solution to Problem

A gas measurement adapter according to the presently disclosed subject matter is a gas measurement adapter including:
a flow tube portion configured to allow gas to pass through the flow tube portion; and
a window portion configured to allow measurement light for measuring a component of the gas passing through the flow tube portion to pass through the window portion, in which the adapter is prepared by using an adapter forming material containing a cycloolefin-based resin as a main component.

Effects of the Invention

According to the presently disclosed subject matter, it is possible to provide a gas measurement adapter prepared by using a thin and moldable adapter forming material which transmits measurement light.

DESCRIPTION OF EMBODIMENTS

Figure 1:
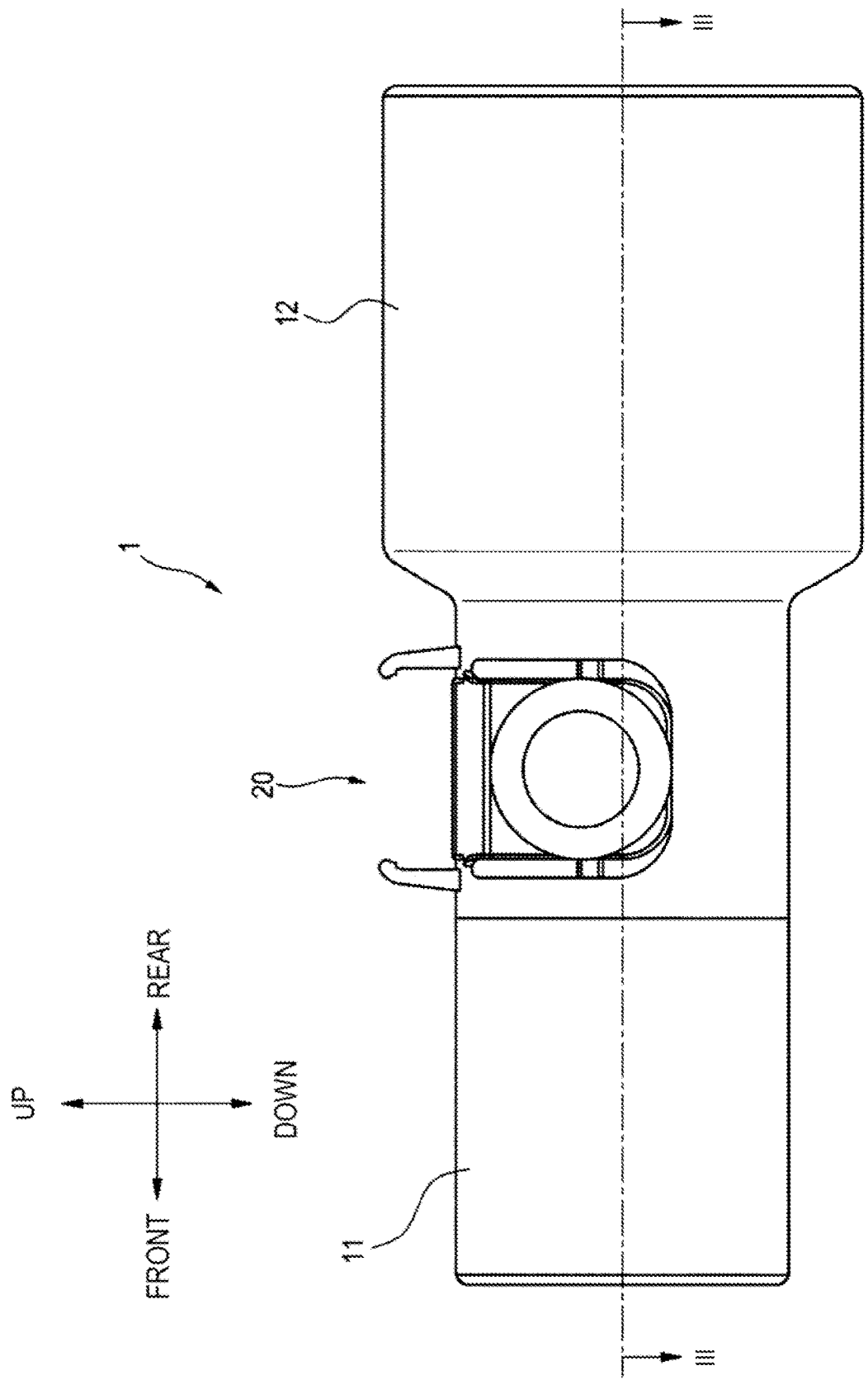
FIG. 1 is a left side view of a gas measurement adapter according to an embodiment of the presently disclosed subject matter.

Hereinafter, an embodiment of the presently disclosed subject matter will be described with reference to the drawings. The terms "upper", "down", "left", "right", "front", and "rear" used in the present description and the drawings are used for convenience to indicate the positional relationship between the members, and do not limit the direction in the actual usage state. In addition, in the description of the drawings, the same elements are denoted by the same reference numerals, and repetitive description thereof will be omitted. Further, the dimensional ratios in the drawings are exaggerated for convenience of explanation and may differ from the actual ratios.

<Gas Measurement Adapter>

A gas measurement adapter according to the presently disclosed subject matter is a gas measurement adapter including: a flow tube portion configured to allow gas to pass through configured to allow gas to pass; and a window portion configured to allow measurement light for measuring a component of the gas passing through the flow tube portion to pass through the window portion. Hereinafter, an embodiment of a typical configuration of the gas measurement adapter according to the presently disclosed subject matter will be briefly described with reference to the drawings, but the configuration of the gas measurement adapter according to the presently disclosed subject matter is not limited to the mode described below.

FIG. 1 is a left side view of a gas measurement adapter 1 according to an embodiment: The gas measurement adapter 1 is an adapter to be used in the case of optically measuring a concentration of a specific component (for example, carbon dioxide) contained in an respiratory gas of a patient requiring respiratory management (hereinafter, also referred to as a subject).

As shown in FIG. 1, the gas measurement adapter 1 includes a first connection adapter 11 provided at a front end portion, a second connection adapter 12 provided at a rear end portion, and a sensor mounting portion 20 provided between the first connection adapter 11 and the second connection adapter 12. A left side surface and a right side surface of the gas measurement adapter 1 are symmetrical.

The first connection adapter 11 is formed in a cylindrical shape, and is connected to an air supply source of an artificial respirator and an exhalation outlet via a connection member such as a Y-shaped tube. The second connection adapter 12 is formed in a cylindrical shape having a diameter larger than that of the first connection adapter 11, and is connected to a device on the subject side such as a tracheal tube or a mask.

Figure 2:
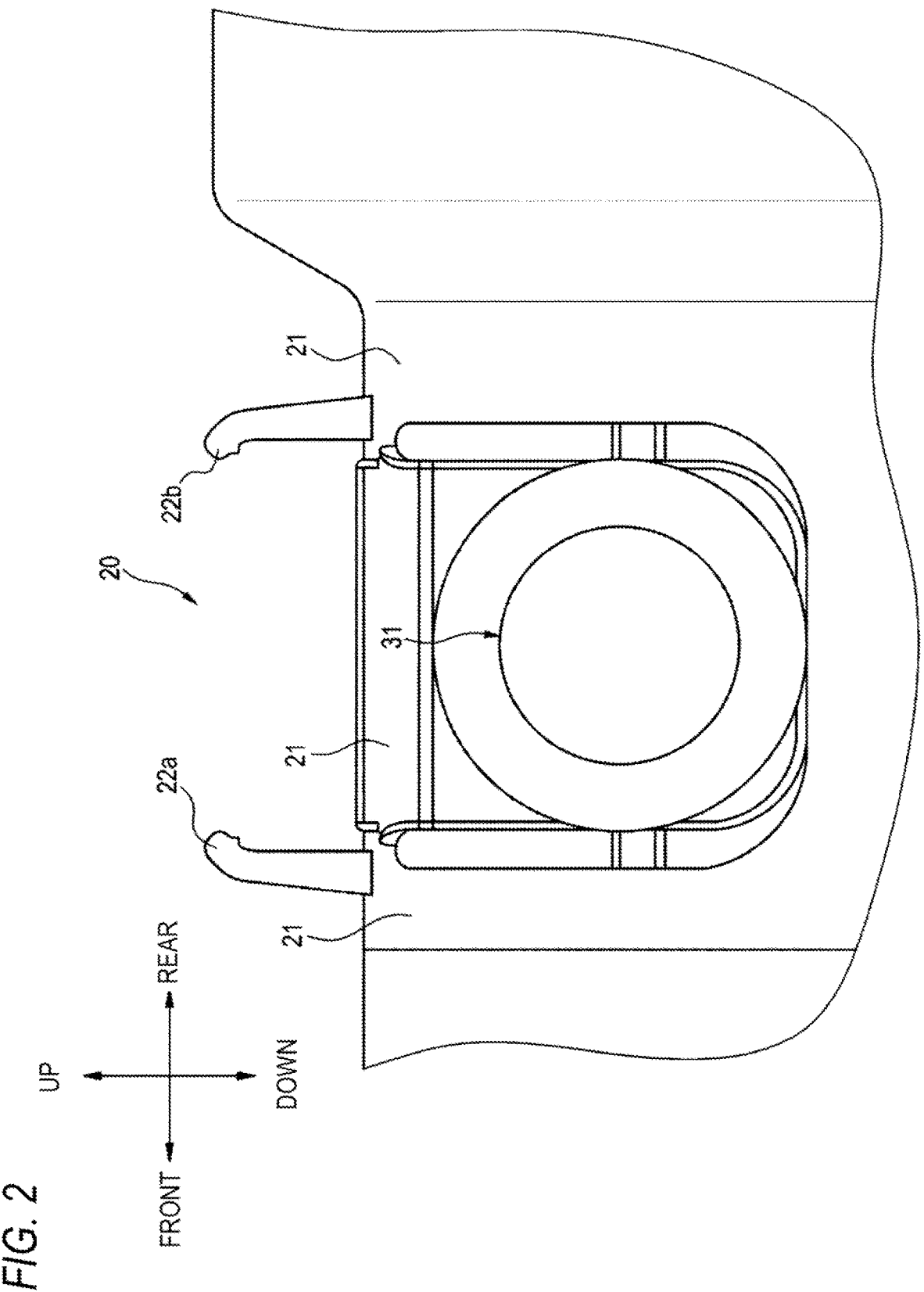
FIG. 2 is a partially enlarged view obtained by enlarging a sensor mounting portion in FIG. 1.

FIG. 2 is a partially enlarged view obtained by enlarging the sensor mounting portion 20 of the gas measurement adapter 1. For example, a respiratory gas concentration sensor (not shown) that optically measures the concentration of a specific gas contained in the respiratory gas of the subject is mounted to the sensor mounting portion 20. As shown in FIG. 2, the sensor mounting portion 20 includes a flow tube portion 21 through which the respiratory gas of the subject passes, and a window portion 31 which is provided at a center portion of the flow tube portion 21.

The flow tube portion 21 is a pipe portion that allows the respiratory gas of the subject flowing from the second connection adapter 12 to pass through an exhalation outlet (not shown) connected to the first connection adapter 11.

The window portion 31 is a window which transmits light (for example, infrared light) for measuring a component of the respiratory gas passing through the flow tube portion 21. The window portion 31 is provided to face a left side surface and a right side surface of the sensor mounting portion 20.

When the respiratory gas concentration sensor is mounted to the sensor mounting portion 20, a light emitter and a light detector provided in the respiratory gas concentration sensor are disposed to face each other in a pair of window portions 31. The respiratory gas concentration sensor mounted to the sensor mounting portion 20 is locked by a pair of locking members 22a and 22b provided facing an upper portion of the sensor mounting portion 20, and is positioned at a predetermined position.

The window portion 31 transmits the measurement light for measuring the component of the respiratory gas. The light radiated from the respiratory gas concentration sensor passes through the window portions 31 disposed facing each other.

The window portion 31 is preferably thinner than the flow tube portion 21. This is because it is easier to transmit effective light (measurement light). Further, the window portion 31 is preferably molded integrally with the flow tube portion 21. This is because the molding man-hours and the processing man-hours may be small, and the strength can be increased by integration. Here, "molded integrally" means that the window portion 31 and the flow tube portion 21 are molded as an integral part by various molding methods. As the molding method, for example, a resin molding method including injection molding can be used. It is sufficient that the window portion 31 and the flow tube portion 21 are prepared by using an adapter forming material according to the presently disclosed subject matter, which has high fluidity in a mold and has an appropriate absorption rate of measurement light.

Figure 3:
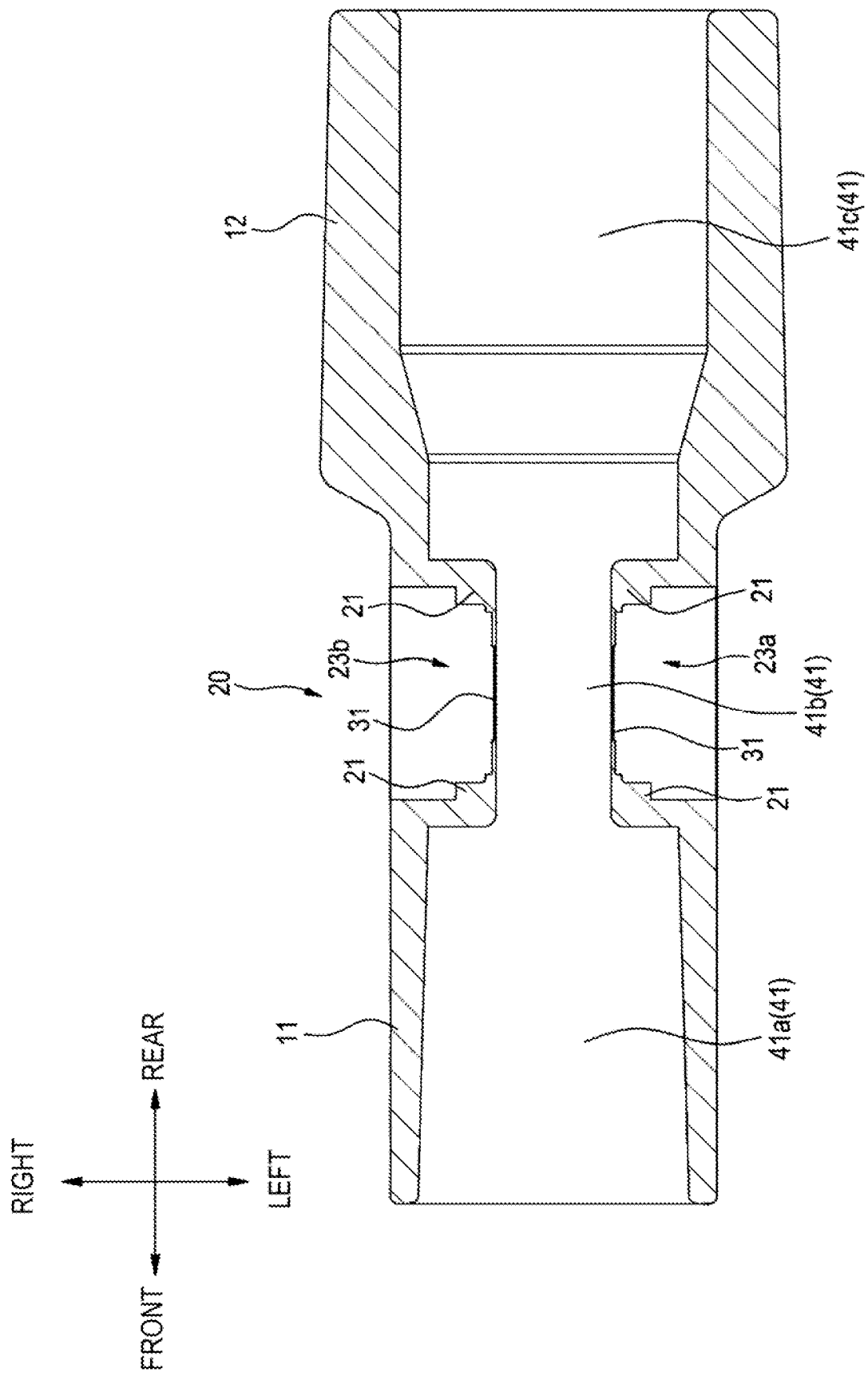
FIG. 3 is a cross-sectional view taken along a line III-III in FIG. 1.

FIG. 3 is a cross-sectional view taken along a line III-III in FIG. 1 and is a cross-sectional view showing an internal configuration of the gas measurement adapter 1. As shown in FIG. 3, a ventilation passage 41 (41a, 41b, 41c) for ventilating the respiratory gas of the subject is formed inside the gas measurement adapter 1. The ventilation passage 41 is formed as, for example, one ventilation passage in which a ventilation passage 41a in the first connection adapter 11, a ventilation passage 41b in the sensor mounting portion 20, and a ventilation passage 41c in the second connection adapter 12 are communicated with each other.

The ventilation passage 41a in the first connection adapter 11, the ventilation passage 41b in the sensor mounting portion 20, and the ventilation passage 41e in the second connection adapter 12 communicate with each other.

The respiratory gas concentration sensor is fitted to fitting portions 23a and 23b of the sensor mounting portion 20. The fitting portions 23a and 23b are each composed of an outer surface of the window portion 31 and an outer surface of the flow tube portion 21 provided around the window portion 31.

<Adapter Forming Material>

The gas measurement adapter according to the presently disclosed subject matter is prepared by using an adapter forming material containing a cycloolefin-based resin as a main component. That is, the adapter forming material according to the embodiment of the presently disclosed subject matter contains a cycloolefin-based resin as a main component. When a thin and moldable adapter forming material which transmits measurement light is used, it is possible to provide a gas measurement adapter which can be easily and integrally prepared. The gas measurement adapter includes a portion (window portion) through which the measurement light for measuring the component of the gas passes and a portion (flow tube portion) through which the gas passes, and when the adapter forming material according to the presently disclosed subject matter is used, a configuration having further excellent moldability can be obtained, as compared with the case where the window portion and the flow tube portion are configured by using a hard resin material (comparison between Example and Comparative Example).

It is preferable that the adapter forming material further contains, as an additive, a (co)polymer having a structural unit derived from an α-olefin. Accordingly, an adapter forming material having toughness can be obtained. Therefore, it is possible to provide a gas measurement adapter having high strength and high toughness.

It is preferable that in the adapter forming material, the content of the cycloolefin-based resin as the main component is 65 mass % to 97 mass %, and the content of the (co)polymer having a structural unit derived from an α-olefin as the additive is 3 mass % to 35 mass %, with respect to a total amount of the main component and the additive. It is more preferable that the content of the cycloolefin-based resin as the main component is 70 mass % to 95 mass %, and the content of the (co)polymer having a structural unit derived from an α-olefin as the additive is 5 mass % to 30 mass %, with respect to the total amount of the main component and the additive. Within the above range, it is possible to obtain an adapter forming material which can transmit measurement light even more, can be molded to be thinner, and has toughness. Therefore, it is possible to provide a gas measurement adapter having higher strength and higher toughness, which can be molded (prepared) more integrally and easily.

The (co)polymer having a structural unit derived from an α-olefin as the additive is preferably a styrene-ethylene/butylene-styrene block copolymer (SEBS). Accordingly, an adapter forming material having toughness can be obtained. Therefore, it is possible to provide a gas measurement adapter having high strength and high toughness.

The styrene content in the SEBS is preferably 5 mass % to 60 mass %. With such a content, an adapter forming material having excellent toughness can be obtained. Therefore, it is possible to provide a gas measurement adapter having higher strength and higher toughness. From the above viewpoints, the styrene content in the SEBS is more preferably 9 mass % to 58 mass %. The styrene content in the SEBS can be measured by infrared spectroscopy (IR), nuclear magnetic resonance (NMR), or the like.

The above cycloolefin-based resin is preferably a cycloolefin copolymer (COC). It is found that the gas measurement adapter includes a portion (window portion) through which the measurement light for measuring the component of the gas passes and a portion (flow tube portion) through which the gas passes, and when the window portion and the flow tube portion are configured by using a hard resin material, the fluidity of the hard resin material is low, the moldability is not sufficient, and integration and thin molding are different (the product yield of the adapter is poor and the cost is high); however, when the cycloolefin-based resin, especially the cycloolefin copolymer (COC) used in the presently disclosed subject matter, has high fluidity and can be formed into a configuration having excellent moldability, can be integrally and thinly molded, and has excellent transparency and high transmittance for infrared light. It is found that when COC is used as the adapter forming material, it is possible to provide a gas measurement adapter in which the window portion and the flow tube portion are integrally formed and which is excellent in moldability and can be easily and integrally prepared. It is considered that the reason why the transmittance of COC for infrared light is high is that COC is transparent and does not have an absorption band in the vicinity of 4.3 μm, which is the absorption band of $CO_2$ molecules.

Hereinafter, each component of the above adapter forming material will be described in more detail.

<Main Component>

It is sufficient that the adapter forming material contains a cycloolefin-based resin as the main component. As the cycloolefin-based resin as the main component, a cycloolefin copolymer (COC) and a cycloolefin polymer (COP) can be used. If necessary, COC and COP may be used in combination.

Examples of the cycloolefin copolymer (COC) and the cycloolefin polymer (COP) include a norbornene polymer, a monocyclic olefin polymer, a cyclic conjugated diene polymer, a vinyl alicyclic hydrocarbon polymer, a hydride of these polymers, and a copolymer thereof. Among these, a cycloolefin copolymer (COC), which has high fluidity, can be integrally and thinly molded, has excellent transparency, and has high transmittance for infrared light, is preferred.

Examples of the method for synthesizing the cycloolefin copolymer (COC) and the cycloolefin polymer (COP) include known synthetic methods represented by the following formulas (1) to (7).

That is,
addition copolymerization of norbornenes (addition copolymerization of norbornenes and α-olefins using highly reactive norbornenes as monomers) represented by formula (1), hydrogenated ring-opening metathesis polymerization of norbornenes represented by formula (2),
transannular reaction of alkylidene norbornenes represented by formula (3),
addition polymerization of norbornenes represented by formula (4),
1,2-addition polymerization, or 1,4-addition polymerization and hydrogenation reaction of cyclopentadiene represented by formula (5),
1,2-addition polymerization, or 1,4-addition polymerization and hydrogenation reaction of cyclohexadiene represented by formula (6), and
cyclic polymerization of conjugated dienes represented by formula (7).

For example, by appropriately selecting $R_1$ and $R_2$ in the formula (2), a hydrogenated ring-opening metathesis polymer of norbornenes having a chemical structure represented by the following A to F can be obtained. Here, the hydrogenated ring-opening metathesis polymer of norbornenes having the chemical structure represented by A below is an example in which both $R_1$ and $R_2$ are hydrogen atoms. The hydrogenated ring-opening metathesis polymer of norbornenes having the chemical structure represented by B below is an example in which $R_1$ is a hydrogen atom and $R_2$ is a phenyl group. The hydrogenated ring-opening metathesis polymer of norbornenes having the chemical structure represented by C below is an example in which $R_1$ is a hydrogen atom and Ra is a cyclohexyl group. The hydrogenated ring-opening metathesis polymer of norbornenes having the chemical structure represented by D below is an example in which $R_2$ and Ra are linked to each other to form a cyclopentane ring. The hydrogenated ring-opening metathesis polymer of norbornenes having the chemical structure represented by E below is an example in which $R_1$ and $R_2$ are linked to each other to form a 6-methyl-norbornane ring as a norbornane (bicyclo[2.2.1]heptane) ring having an alkyl group. The hydrogenated ring-opening metathesis polymer of norbornenes having the chemical structure represented by F below is an example in which $R_1$ and $R_2$ are linked to each other to form a norbornane ring. Same or similarly, polymers having different chemical structures can be obtained by appropriately selecting $R_1$, $R_2$, and Ra in the formula (1), $R_1$ and $R_2$ in the formula (4), and R in the formula (7). That is, by designing the type of substituent (further, molecular weight distribution or the like), properties such as impact resistance and stretchability can be enhanced or imparted.

[Chem. 1]

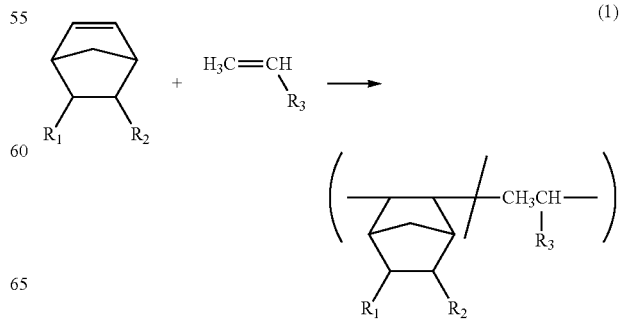

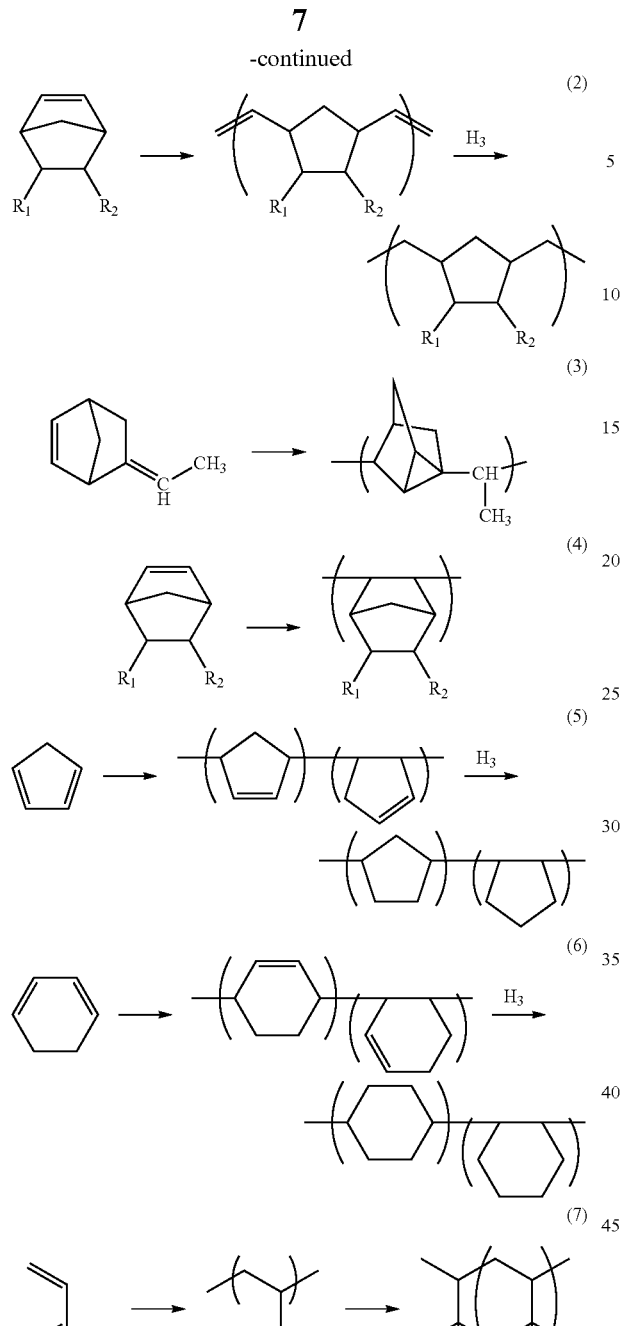

commercially available product of the cycloolefin copolymer (COC) include: TOPAS® 5013, 8007, 6017, 6015, 6013, 9506 manufactured by Topas Advanced Polymers GmbH; and APEL® 6509T, 6011T, 6013T, 6015T, 5014DP, 5014CL manufactured by Mitsui Chemicals, Inc. Among these, TOPAS® 5013, 8007 and APEL® 6509T are preferred. For example, TOPAS® is a copolymer represented by the following formula (1a), which is obtained by copolymerizing norbornene synthesized from dicyclopentadiene and ethylene and ethylene using a metallocene catalyst (one type of the copolymer represented by the above formula (1)). APEL® is a copolymer represented by the following formula (1b) (one type of the copolymer represented by the above formula (1)). TOPAS® (the copolymer represented by the following formula (1a)) and APEL® (the copolymer represented by the following formula (1b)) are preferred because of having high fluidity, being integrally and thinly molded, having excellent transparency, and having high transmittance for infrared light. Examples of $R_1$ and $R_2$ in the formula (1b) include substituents such as a hydrogen atom, an alkyl group, a phenyl group, an alkylphenyl group, a cycloalkyl group, a cycloolefin ring group formed by linking $R_1$ and $R_2$ to each other, a cycloolefin ring group having an alkyl group, a norbornane ring group, and a norbornane ring group having an alkyl group, which are, independent of each other, represented by the above A to F exemplified as $R_1$ and $R_2$ in the above formula (2), but is not limited thereto.

[Chem. 3]

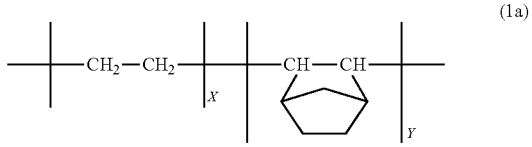

(1a)

[Chem. 4]

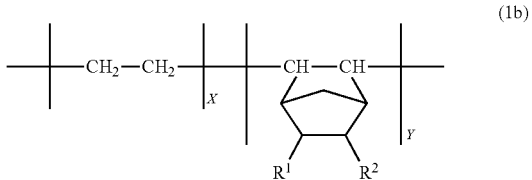

(1b)

Examples of the commercially available product of the cycloolefin polymer (COP) include ZEONOR® 1060R, 1020R manufactured by Nippon Zeon Corporation.

When the above commercially available products are not used and the cycloolefin copolymer (COC) and the

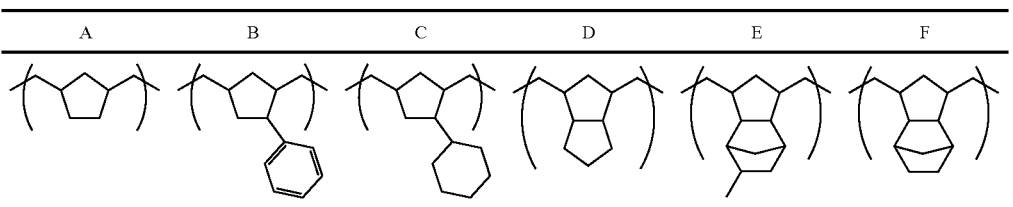

The cycloolefin copolymer (COC) and the cycloolefin polymer (COP) may be prepared by using a known synthetic method as described above, or a commercially available product thereof may be used. Among these, examples of the cycloolefin polymer (COP) are to be prepared by using a known synthetic method, methods described in the following publications can be used, but the presently disclosed subject matter is not limited thereto. The cycloolefin copolymer (COC) and the cycloolefin polymer (COP) can be produced by using, for example, methods described in JPH08-012712A (method for producing cycloolefin copolymer), JPH07-224122A (cycloolefin copolymer and production method therefor), JPH06-271628A (method for producing cycloolefin copolymer), JPH06-271627A (method for producing cycloolefin copolymer), JP2020-066683A (norbornene-based ring-opening polymer hydride, resin composition and molded body), republication of WO2016/143424 (syndiotactic crystalline dicyclopentadiene ring-opening polymer hydride, syndiotactic dicyclopentadiene ring-opening polymer, and production method therefor), and JP2015-086288A (cycloolefin monomer, polymerizable composition, resin molded body, crosslinkable resin molded body and crosslinked resin molded body), but is not limited thereto.

The content of the "main component" in the adapter forming material is sufficiently 50 mass % or more, and is preferably 65 mass % to 97 mass % as described above, and more preferably 70 mass % to 95 mass %, with respect to the total amount of the main component and the additive.

<Additive>

It is preferable that the adapter forming material further contains, as an additive, a (co)polymer having a structural unit derived from an α-olefin, in addition to the cycloolefin-based resin as the main component. Examples of the (co)polymer having a structural unit derived from an α-olefin include a styrene-ethylene/butylene-styrene block copolymer (SEBS), an ethylene propylene diene rubber (EPDM), a modified polyolefin, a low density polyethylene (LDPE), an ethylene-methacrylic acid copolymer, and a hydrogenated styrene butadiene rubber (HSBR). From the viewpoint of imparting excellent elasticity and toughness, a styrene-ethylene/butylene-styrene block copolymer (SEBS) is preferred.

The styrene content in the SEBS and the content of the (co)polymer having a structural unit derived from an α-olefin as the additive with respect to the total amount of the main component and the additive are as described above.

The (co)polymer having a structural unit derived from α-olefin may be prepared by using a known synthetic method, or a commercially available product thereof may be used. Examples of the commercially available product of the (co)polymer having a structural unit derived from an α-olefin include, as the (hydrogenated) styrene-ethylene/butylene-styrene block copolymer (SEBS), DYNARON® 8300P (styrene content: 9 mass %), 8600P (styrene content: 15 mass %), 8903P (styrene content: 35 mass %), 9901P (styrene content: 53 mass %) manufactured by JSR CORPORATION, and A1536 (styrene content: 42 mass %), A1535 (styrene content: 58 mass %) manufactured by KRATON CORPORATION. Examples thereof include, as the ethylene propylene diene rubber (EPDM), Mitsui EPT X-3012P manufactured by Mitsui Chemicals, Inc. Examples thereof include, as the ethylene-methacrylic acid copolymer, NUCREL products such as NUCREL AN4213C manufactured by DOW-MITSUI POLYCHEMICALS CO., LTD. Examples thereof include, as the low density polyethylene (LDPE), Novatec® LD LJ902 manufactured by Japan Polyethylene Corporation.

When the above commercially available products are not used and the (co)polymer having a structural unit derived from an α-olefin is to be produced by using a known synthetic method, methods described in the following publications can be used, but the presently disclosed subject matter is not limited thereto. For example, for the styrene-ethylene/butylene-styrene block copolymer (SEBS), a method described in Paragraphs "0015" to "0016" of JP2004-083622A (rubber composition and production method therefor, and rubber molded product and production method therefor) can be used. Specifically, reaction conditions in a method of hydrogenating the styrene-ethylene/butylene-styrene block copolymer (SEBS) are not particularly limited, and the hydrogenation is carried out generally at 20° C. to 150° C. under hydrogen pressurization of 0.1 MPa to 10 MPa in the presence of a hydrogenation catalyst. In this case, a hydrogenation rate can be optionally selected by changing the amount of the hydrogenation catalyst, the hydrogen pressure or the reaction time during the hydrogenation reaction, and the like. As the above hydrogenation catalyst, a compound containing any metal element of Group 11, Group 4, Group 5, Group 6, Group 7, Group 8, Group 9, and Group 10 in the periodic table of elements, for example, a compound containing a Ti, V, Co, Ni, Zr, Ru, Rh, Pd, Hf, Re, or Pt atom can be used. Specific examples of the above hydrogenation catalyst include a metallocene compound containing Ti, Zr. Hf, Co, Ni, Pd, Pt, Ru, Rh, or Re, a supported heterogeneous catalyst in which a metal such as Pd, Ni, Pt, Rh, or Ru is supported on a carrier such as carbon, silica, alumina, or diatomaceous earth, a homogeneous Ziegler-type catalyst that combines an organic salt of a metal element such as Ni or Co or an acetylacetone salt with a reducing agent such as organic aluminum, an organometallic compound or complex such as Ru and Rh, and fullerene and carbon nanotube occluded with hydrogen. Among these, a metallocene compound containing any one of Ti, Zr, Hf, Co, and Ni is preferred because of being capable of being hydrogenated in a homogeneous system in an inert organic solvent. A metallocene compound any one of Ti, Zr, and Hf is more preferred. A hydrogenation catalyst obtained by reacting a titanocene compound with an alkyllithium is particularly preferred because of being an inexpensive and industrially particularly useful catalyst. Specific examples of the hydrogenation catalyst includes hydrogenation catalysts described in JPH01-275605A, JPH05-271326A, JPH05-271325A, JPHOS-222115A, JPH11-292924A, JP2000-037632A, JPS59-133203A, JPS63-005401A, JPS62-218403A, JPH07-090017A, JPS43-019960B, and JPS47-040473B. Only one type of the hydrogenation catalyst may be used, or two or more types may be used in combination.

In addition, for the method for producing the styrene-ethylene/butylene-styrene block copolymer (SEBS), a method described in Paragraphs "0032" to "0049" of JP2015-513584T (highly fluid hydrogenated styrene-butadiene-styrene block copolymer and use thereof) can also be used. Among these, the hydrogenation of a selectively hydrogenated low viscosity styrene-butadiene-styrene (hydrogenated styrene-ethylene/butylene-styrene block copolymer; SEBS) can be carried out by either some of the hydrogenation methods known in the related art or a selective hydrogenation method. Such hydrogenation can be performed by using methods disclosed in U.S. Pat. No. 3,595,942 specification; U.S. Pat. No. 3,634,549 specification; U.S. Pat. No. 3,670,054 specification; and U.S. Pat. No. 3,700,633 specification. These methods are based on the action of a catalyst suitable for hydrogenation of a polymer containing an aromatic ring or an ethylenically unsaturated bond. It is preferable that such a catalyst or catalyst precursor contains alkyl aluminum or a metal selected from Group 1, Group 2, or Group 3 in the periodic table of elements, and particularly a metal of Group 8, Group 9, or Group 10 such as nickel or cobalt, which is to be combined with a reducing agent suitable for a lithium, magnesium or aluminum hydride. The preparation can be carried out in a suitable solvent or diluent at a temperature of 20° C. to 80° C. Examples of other useful catalysts include titanium-based catalysts.

The (co)polymer having a structural unit derived from an α-olefin other than the styrene-ethylene/butylene-styrene block copolymer (SEBS) can also be produced by using a known method.

Other Additives

The adapter forming material may contain additives other than the main component and the (co)polymer having a structural unit derived from an α-olefin as the additive, for example, a colorant, a stabilizer, and an inorganic filler within a range not impairing the effects of the presently disclosed subject matter. Specific examples of the colorant include dyes and pigments such as cadmium sulfide, phthalocyanine, and carbon black. Examples of the stabilizer include: antioxidants and heat stabilizers such as hindered phenol, hydroquinone, thioether, phosphites and substitutions and combinations thereof; UV absorbers such as resorcinol, salicylate, benzotriazole, and benzophenone; various lubricants and mold release agents including higher fatty acids such as stearic acid and montanic acid and metal salts thereof, esters, half esters, derivatives of stearyl alcohol; flame retardant aids such as antimony oxide; antistatic agents such as sodium dodecylbenzenesulfonate and polyalkylene glycol; crystallization accelerators; and silane coupling agents. Examples of the inorganic filler include fibrous inorganic fillers such as glass fibers, carbon fibers, and ceramic fibers, and granular, powdery, plate-like inorganic fillers such as mica, glass beads, silica, barium titanate, hydrotalcite, and zeolite. The blending amount of other additives is appropriately determined in consideration of various properties of the main component and the additive.

The presently disclosed subject matter is not limited to the above embodiment and may be modified or improved as appropriate. Shapes, sizes, numerical values, forms, numbers, arrangement places, and the like of components in the above embodiment are optional and not limited as long as the presently disclosed subject matter can be achieved.

EXAMPLES

<Sample Preparation>

When the cycloolefin-based resin as a main component and the (co)polymer having a structural unit derived from an α-olefin as an additive were used in Examples shown below, both were melt-kneaded using an extruder. Then, each sample was prepared by injection-molding the melt-kneaded material using an injection molding machine or the like. Among Examples, when the (co)polymer having a structural unit derived from α-olefin as an additive was not used and the cycloolefin-based resin as a main component was used alone, kneading did not need to be performed (no need for an extruder). Therefore, each sample was prepared by melting (heating) and injection-molding a resin material of the main component using an injection molding machine or the like. In Examples and Comparative Examples shown below, when the additive was used in combination, an extruder was used to melt-knead the main component and the additive in a mixing ratio shown in Table 1. When no additive was used, only the main component shown in Table 1 was used. Thereafter, molding was performed by injecting the material into a mold of the gas measurement adapter shown in FIG. 1, and a sample of the gas measurement adapter shown in FIG. 1 was prepared. The details will be described below.

Example 1-1

An injection molding machine (trade name: injection molding machine LA40, manufactured by Sodick) was used, and the cycloolefin-based resin shown below was used alone as the main component of the adapter forming material. The adapter forming material containing the cycloolefin-based resin as a main component was charged into the injection molding machine, heated and melted, and then injected into the mold of the gas measurement adapter shown in FIG. 1 for molding, thereby preparing a gas measurement adapter sample 1-1.

For the cycloolefin-based resin as a main component of the adapter forming material in Example 1-1, a cycloolefin copolymer (COC), APEL® 6509T (an addition copolymer of norbornenes and α-olefin and represented by the above formula (1b)) manufactured by Mitsui Chemicals, Inc. was used.

Example 1-2

As the adapter forming material, 90 mass % of the cycloolefin-based resin as a main component and 10 mass % of the (co)polymer having a structural unit derived from an α-olefin as an additive were used in combination. The adapter forming material consisting of the main component and the additive was melt-kneaded using an extruder. Thereafter, molding was performed by injecting the melt-kneaded material into the mold of the gas measurement adapter shown in FIG. 1 using the injection molding machine same as in Example 1-1, thereby preparing a gas measurement adapter sample 1-2.

As the cycloolefin-based resin, the product same as in Example 1-1 was used. As the (co)polymer having a structural unit derived from an α-olefin as an additive, DYNARON® 8300P (styrene content: 9 mass %) manufactured by JSR CORPORATION, i.e., a styrene-ethylene/butylene-styrene block copolymer (SEBS), was used.

Example 1-3

A gas measurement adapter sample 1-3 was prepared in the same manner as in Example 1-2, except that as the styrene-ethylene/butylene-styrene block copolymer (SEBS) as an additive, DYNARON® 8600P (styrene content: 15 mass %) manufactured by JSR CORPORATION was used instead of DYNARON® 8300P.

Example 1-4

A gas measurement adapter sample 1-4 was prepared in the same manner as in Example 1-2, except that the mixing ratio of the main component and the additive was changed to 95 mass % of the main component and 5 mass % of the additive, and as the styrene-ethylene/butylene-styrene block copolymer (SEBS) as an additive, DYNARON® 8903 (styrene content: 35 mass %) manufactured by JSR CORPORATION was used instead of DYNARON® 8300P.

Example 1-5

A gas measurement adapter sample 1-5 was prepared in the same manner as in Example 1-4, except that the mixing ratio of the main component and the additive was changed to 90 mass % of the main component and 10 mass % of the additive.

Example 1-6

A gas measurement adapter sample 1-6 was prepared in the same manner as in Example 1-2, except that the mixing ratio of the main component and the additive was changed to 95 mass % of the main component and 5 mass % of the additive, and as the styrene-ethylene/butylene-styrene block copolymer (SEBS) as an additive, DYNARON® 9901 (styrene content: 53 mass %) manufactured by JSR CORPORATION was used instead of DYNARON® 8300P.

Example 1-7

A gas measurement adapter sample 1-7 was prepared in the same manner as in Example 1-6, except that the mixing ratio of the main component and the additive was changed to 90 mass % of the main component and 10 mass % of the additive.

Example 1-8

A gas measurement adapter sample 1-8 was prepared in the same manner as in Example 1-6, except that the mixing ratio of the main component and the additive was changed to 85 mass % of the main component and 15 mass % of the additive.

Example 1-9

A gas measurement adapter sample 1-9 was prepared in the same manner as in Example 1-2, except that the mixing ratio of the main component and the additive was changed to 95 mass % of the main component and 5 mass % of the additive, and as the styrene-ethylene/butylene-styrene block copolymer (SEBS) as an additive, A1536 (styrene content: 42 mass %) manufactured by KRATON CORPORATION was used instead of DYNARON® 8300P.

Example 1-10

A gas measurement adapter sample 1-10 was prepared in the same manner as in Example 1-9, except that the mixing ratio of the main component and the additive was changed to 90 mass % of the main component and 10 mass % of the additive.

Example 1-11

A gas measurement adapter sample 1-11 was prepared in the same manner as in Example 1-2, except that as the styrene-ethylene/butylene-styrene block copolymer (SEBS) as an additive, A1535 (styrene content: 58 mass %) manufactured by KRATON CORPORATION was used instead of DYNARON® 8300P.

Example 1-12

A gas measurement adapter sample 1-12 was prepared in the same manner as in Example 1-11, except that the mixing ratio of the main component and the additive was changed to 85 mass % of the main component and 15 mass % of the additive.

Example 1-13

A gas measurement adapter sample 1-13 was prepared in the same manner as in Example 1-2, except that as an additive, Mitsui EPT X-3012P manufactured by Mitsui Chemicals, Inc., i.e., an ethylene propylene diene rubber (EPDM), was used instead of DYNARON® 8300P.

Example 1-14

A gas measurement adapter sample 1-14 was prepared in the same manner as in Example 1-2, except that as an additive, NUCREL AN4213C manufactured by DOW-MITSUI POLYCHEMICALS CO., LTD., i.e., an ethylene-methacrylic acid copolymer, was used instead of DYNARON® 8300P.

Example 1-15

A gas measurement adapter sample 1-15 was prepared in the same manner as in Example 1-2, except that as an additive, Novatec® LD LJ902 manufactured by Japan Polyethylene Corporation, i.e., a low density polyethylene (LDPE), was used instead of DYNARON® 8300P.

Example 2-1

The following cycloolefin-based resin was used alone as the adapter forming material. The adapter forming material containing the cycloolefin-based resin was charged into the injection molding machine same as in Example 1-1, heated and melted, and then injected into the mold of the gas measurement adapter shown in FIG. 1 for molding, thereby preparing a gas measurement adapter sample 2-1.

As the cycloolefin-based resin, TOPAS® 8007 (one type of the copolymer represented by the above formula (1a) and obtained by copolymerizing norbornene synthesized from dicyclopentadiene and ethylene and ethylene using a metallocene catalyst) manufactured by Topas Advanced Polymers GmbH, i.e., a cycloolefin copolymer (COC), was used.

Example 2-2

As the adapter forming material, 95 mass % of the cycloolefin-based resin as a main component and 5 mass % of the (co)polymer having a structural unit derived from an α-olefin as an additive were used in combination. The adapter forming material consisting of the main component and the additive was melt-kneaded using the extruder same as Example 1-2. Thereafter, molding was performed by injecting the melt-kneaded material into the mold of the gas measurement adapter shown in FIG. 1 using the injection molding machine same as in Example 1-1, thereby preparing a gas measurement adapter sample 2-2.

As the cycloolefin-based resin, the product same as in Example 2-1 was used. As the (co)polymer having a structural unit derived from an α-olefin as an additive, DYNARON® 8903 (styrene content: 35 mass %) manufactured by JSR CORPORATION, i.e., a styrene-ethylene/butylene-styrene block copolymer (SEBS), was used.

Example 2-3

A gas measurement adapter sample 2-3 was prepared in the same manner as in Example 2-2, except that as the styrene-ethylene/butylene-styrene block copolymer (SEBS) as an additive, DYNARON® 9901 (styrene content: 53 mass %) manufactured by JSR CORPORATION was used instead of DYNARON® 8300P.

Example 2-4

A gas measurement adapter sample 2-4 was prepared in the same manner as in Example 2-3, except that the mixing ratio of the main component and the additive was changed to 90 mass % of the main component and 10 mass % of the additive.

Example 2-5

A gas measurement adapter sample 2-5 was prepared in the same manner as in Example 2-3, except that the mixing ratio of the main component and the additive was changed to 85 mass % of the main component and 15 mass % of the additive.

Example 2-6

A gas measurement adapter sample 2-6 was prepared in the same manner as in Example 2-2, except that as the styrene-ethylene/butylene-styrene block copolymer (SEBS) as an additive, A1536 (styrene content: 42 mass %) manufactured by KRATON CORPORATION was used instead of DYNARON® 8903.

Example 2-7

A gas measurement adapter sample 2-7 was prepared in the same manner as in Example 2-2, except that the mixing ratio of the main component and the additive was changed to 85 mass % of the main component and 15 mass % of the additive, and as the styrene-ethylene/butylene-styrene block copolymer (SEBS) as an additive, A1535 (styrene content: 58 mass %) manufactured by KRATON CORPORATION was used instead of DYNARON® 8903.

Example 3-1

The following cycloolefin-based resin was used alone as the adapter forming material. The adapter forming material containing the cycloolefin-based resin as a main component was charged into the injection molding machine same as in Example 1-1, heated and melted, and then injected into the mold of the gas measurement adapter shown in FIG. 1 for molding, thereby preparing a gas measurement adapter sample 3-1.

As the cycloolefin-based resin, TOPAS® 5013 (one type of the copolymer represented by the above formula (1a) and obtained by copolymerizing norbornene synthesized from dicyclopentadiene and ethylene and ethylene using a metallocene catalyst) manufactured by Topas Advanced Polymers GmbH, i.e., a cycloolefin copolymer (COC), was used.

Example 3-2

As the adapter forming material, 70 mass % of the cycloolefin-based resin as a main component and 30 mass % of the (co)polymer having a structural unit derived from an α-olefin as an additive were used in combination. The adapter forming material consisting of the main component and the additive was melt-kneaded using the extruder same as Example 1-2. Thereafter, molding was performed by injecting the melt-kneaded material into the mold of the gas measurement adapter shown in FIG. 1 using the injection molding machine same as in Example 1-1, thereby preparing a gas measurement adapter sample 3-2.

As the cycloolefin-based resin, the product same as in Example 3-1 was used. As the (co)polymer having a structural unit derived from an α-olefin as an additive, DYNARON® 901 (styrene content in SEBS: 53 mass %)  manufactured by JSR CORPORATION, i.e., a styrene-ethylene/butylene-styrene block copolymer (SEBS), was used.

Example 4

The following cycloolefin-based resin was used alone as the adapter forming material. The adapter forming material containing the cycloolefin-based resin was charged into the injection molding machine same as in Example 1-1, heated and melted, and then injected into the mold of the gas measurement adapter shown in FIG. 1 for molding, thereby preparing a gas measurement adapter sample 4.

As the cycloolefin-based resin, ZEONOR® 1060R manufactured by Nippon Zeon Corporation, i.e., a cycloolefin polymer (COP), was used.

Example 5

The following cycloolefin-based resin was used alone as the adapter forming material. The adapter forming material containing the cycloolefin-based resin was charged into the injection molding machine same as in Example 1-1, heated and melted, and then injected into the mold of the gas measurement adapter shown in FIG. 1 for molding, thereby preparing a gas measurement adapter sample 5.

As the cycloolefin-based resin, ZEONOR® 1020R manufactured by Nippon Zeon Corporation, i.e., a cycloolefin polymer (COP), was used.

Comparative Example 1

As the adapter forming material, an existing hard resin material was used. The adapter forming material containing the hard resin material was charged into the injection molding machine same as in Example 1-1, heated and melted, and then injected into the mold of the gas measurement adapter shown in FIG. 1 for molding, thereby preparing a gas measurement adapter comparison sample 1.

As the hard resin material, Eastar copolyester DN011 manufactured by Eastman Chemical Company, i.e., a PETG resin (a polymer in which about 30% to 40% of EG in PET resin was replaced with cyclohexanedimethanol; glycol-modified polyethylene terephthalate), was used.

<Evaluation on Moldability>

It was visually confirmed that the window portion (diameter: 5.5 mm, thickness: 0.12 mm) of the gas measurement adapter sample obtained in Examples and Comparative Examples could be molded.

Evaluation Criteria for Moldability
- ○: The yield of the product is good, and even when the sample is integrally and thinly molded, the thin window portion can be molded into a sufficient shape (accuracy) in all the samples (10 samples; n=10).
- x: The yield of the product is poor, and the window portion cannot be molded into a sufficient shape (accuracy) in many samples (10 samples; n=10) due to insufficient fluidity due to the integral and thin molding.

<Evaluation on Transmittance for Infrared Light>

When a sensor was installed in the sensor mounting portion of the gas measurement adapter sample obtained in Examples and Comparative Examples, the intensity of infrared light of 4.27±0.01 μm transmitted through the window portion (effective portion) was measured. Comparative Example 1 in which the window portion could not be molded into a sufficient shape (accuracy) could not be evaluated, and therefore, was recorded as "cannot be evaluated" in Table 1.

Evaluation criteria for transmittance for infrared light Table 1 shows the ratio when COC (APEL6509T) is 1.00. 0.90 or more was evaluated as pass.

<Evaluation on Impact and Dropping Resistance>

The sample prepared in Examples and Comparative Examples was subjected to a drop test under the following conditions, and it was visually confirmed that there was no damage (cracks, broken locking members (claw), etc.) after the test. Comparative Example 1 in which the window portion could not be molded into a sufficient shape (accuracy) could not be evaluated, and therefore, was recorded as "cannot be evaluated" in Table 1.

[Test Conditions]

Drop height: 122 cm

Number of drops: 26 in total

Drop method: in all 26 drops, the second connection adapter 12 side in FIG. 1 was held by a hand, the height of the sample (up to the lowermost end) was adjusted to 122 cm, and then the sample was released and freely dropped.

Number of samples: 3 (n=3)

Evaluation criteria for impact and dropping resistance

Number of damages: 0: very good impact resistance during dropping

Number of damages: 1: good impact resistance during dropping

Number of damages: 2: slightly good impact resistance during dropping

Number of damages: 3: poor impact resistance during dropping

Table 1 shows the number of damages from no damage (0) to 3 regarding the impact and dropping resistance.

<Evaluation on Color>

For the samples prepared in Examples and Comparative Examples, the flow tube portion (a portion having a thickness of 3.5 mm) was visually evaluated in two stages of visible and invisible. The results are shown in Table 1. Even in Comparative Example 1 in which the window portion could not be molded into a sufficient shape (accuracy), the flow tube portion could be evaluated, so the color was evaluated.

Regarding the evaluation on color, the sample can be used without any problem even if it is invisible (white). However, it is better to be able to visually observe the inside of the adapter all the time, because it is easier to find a damage such as cracks when the damage occurs inside the adapter. From such a viewpoint, visible (colorless and transparent) ones are preferred.

TABLE 1

| | Adapter forming material | | | | | | Impact and | |
|---|---|---|---|---|---|---|---|---|
| | Main component | | Additive | | | | dropping | |
| | Type | Content (mass %) | Type | Content (mass %) | Styrene content (mass %) in SEBS | Moldability | Transmittance for infrared light | resistance (number of damages) | Color Thickness; 3.5 mm |
| Example 1-1 | COC (APEL 6509) | 100 | — | — | — | ○ | 1.00 | 3 | Visible |
| Example 1-2 | COC (APEL 6509) | 90 | SEBS (DYNARON 8300P) | 10 | 9 | ○ | 1.03 | 0 | Invisible |
| Example 1-3 | COC (APEL 6509) | 90 | SEBS (DYNARON 8600P) | 10 | 15 | ○ | 1.04 | 0 | Invisible |
| Example 1-4 | COC (APEL 6509) | 95 | SEBS (DYNARON 8903P) | 5 | 35 | ○ | 1.03 | 0 | Invisible |
| Example 1-5 | COC (APEL 6509) | 90 | SEBS (DYNARON 8903P) | 10 | 35 | ○ | 1.05 | 0 | Invisible |
| Example 1-6 | COC (APEL 6509) | 95 | SEBS (DYNARON 9901P) | 5 | 53 | ○ | 1.02 | 1 | Visible |
| Example 1-7 | COC (APEL 6509) | 90 | SEBS (DYNARON 9901P) | 10 | 53 | ○ | 1.02 | 0 | Visible |
| Example 1-8 | COC (APEL 6509) | 85 | SEBS (DYNARON 9901P) | 15 | 53 | ○ | 1.03 | 0 | Visible |
| Example 1.9 | COC (APEL 6509) | 95 | SEBS (KRATON A1536) | 5 | 42 | ○ | 1.02 | 2 | Visible |
| Example 1-10 | COC (APEL 6509) | 90 | SEBS (KRATON A1536) | 10 | 42 | ○ | 1.04 | 0 | Visible |
| Example 1-11 | COC (APEL 6509) | 90 | SEBS (KRATON A1535) | 10 | 58 | ○ | 1.02 | 0 | Visible |
| Example 1-12 | COC (APEL 6509) | 85 | SEBS (KRATON A1535) | 15 | 58 | ○ | 1.03 | 0 | Visible |
| Example 1-13 | COC (APEL 6509) | 90 | EPDM (Mitsui EPT X-3012P) | 10 | — | ○ | 0.99 | 0 | Invisible |
| Example 1-14 | COC (APEL 6509) | 90 | Ethylene-methacrylic acid copolymer (NUCREL) | 10 | — | ○ | 1.91 | 2 | Invisible |
| Example 1-15 | COC (APEL 6509 ) | 90 | LDPE (Novatec LD LJ902) | 10 | — | ○ | 0.98 | 2 | Invisible |
| Example 2-1 | COC (TOPAS 8007) | 100 | — | — | — | ○ | 1.00 | 3 | Visible |
| Example 2-2 | COC (TOPAS 8007) | 95 | SEBS (DYNARON 8903P) | 5 | 35 | ○ | 1.00 | 2 | Visible |
| Example 2-3 | COC (TOPAS 8007) | 95 | SEBS (DYNARON 9901P) | 5 | 53 | ○ | 0.97 | 2 | Visible |

TABLE 1-continued

| | Adapter forming material | | | | | | Impact and | |
|---|---|---|---|---|---|---|---|---|
| | Main component | | Additive | | Styrene content | | | dropping resistance | Color |
| | Type | Content (mass %) | Type | Content (mass %) | (mass %) in SEBS | Moldability | Transmittance for infrared light | (number of damages) | Thickness; 3.5 mm |
| Example 2-4 | COC (TOPAS 8007) | 90 | SEBS (DYNARON 9901?) | 10 | 53 | ○ | 0.99 | 1 | Visible |
| Example 2-5 | COC (TOPAS 8007) | 85 | SEBS (DYNARON 9901P) | 15 | 53 | ○ | 1.00 | 0 | Visible |
| Example 2-6 | COC (TOPAS 8007) | 95 | SEBS (KRATON A 1536) | 5 | 42 | ○ | 0.98 | 2 | Visible |
| Example 2-7 | COC (TOPAS 8007) | 85 | SEBS (KRATON A1535) | 15 | 58 | ○ | 0.96 | 0 | Visible |
| Example 3-1 | COC (TOPAS 5013) | 100 | — | — | — | ○ | 1.00 | 3 | Visible |
| Example 3-2 | COC (TOPAS 5013) | 70 | SEBS (DYNARON 9901P) | 30 | 53 | ○ | 1.00 | 1 | Visible |
| Example 4 | COP (ZEONOR 1060R) | 100 | — | — | — | ○ | 1.00 | 3 | Visible |
| Example 5 | COP (ZEONOR 1020R) | 100 | — | — | — | ○ | 1.00 | 3 | Visible |
| Comparative Example 1 | PETG (Bastar DN011) | 100 | — | — | — | x | Cannot be evaluated | Cannot be evaluated | Visible |

INDUSTRIAL APPLICABILITY

According to the presently disclosed subject matter, it is possible to provide a gas measurement adapter prepared by using a thin and moldable adapter forming material which transmits measurement light.

The invention claimed is:

1. A gas measurement adapter comprising:
   a flow tube portion configured to allow gas to pass through the flow tube portion; and
   a window portion configured to allow measurement light for measuring a component of the gas passing through the flow tube portion to pass through the window portion, wherein
   the adapter is prepared by using an adapter forming material containing a cycloolefin-based resin as a main component;
   wherein the adapter forming material further contains, as an additive, a (co)polymer having a structural unit derived from an α-olefin; and
   wherein the cycloolefin-based resin as the main component is 65 mass % to 97 mass %, and the (co)polymer having a structural unit derived from an α-olefin as the additive is 3 mass % to 35 mass %, with respect to a total amount of the main component and the additive.

2. The gas measurement adapter according to claim 1, wherein the (co)polymer having a structural unit derived from an α-olefin as the additive is a styrene-ethylene/butylene-styrene block copolymer.

3. The gas measurement adapter according to claim 2, wherein a styrene content in the styrene-ethylene/butylene-styrene block copolymer is 5 mass % to 60 mass %.

4. The gas measurement adapter according to claim 1, wherein the cycloolefin-based resin as the main component is a cycloolefin copolymer.

5. The gas measurement adapter according to claim 1, wherein the window portion is thinner than the flow tube portion.

6. The gas measurement adapter according to claim 1, wherein the window portion is molded integrally with the flow tube portion.

7. An adapter forming material comprising:
   a cycloolefin-based resin as a main component; and
   as an additive, a (co)polymer having a structural unit derived from an α-olefin;
   wherein the cycloolefin-based resin as the main component is 65 mass % to 97 mass %, and the (co)polymer having a structural unit derived from an α-olefin as the additive is 3 mass % to 35 mass %, with respect to a total amount of the main component and the additive.

8. A gas measurement adapter comprising:
   a flow tube portion configured to allow gas to pass through the flow tube portion; and
   a window portion configured to allow measurement light for measuring a component of the gas passing through the flow tube portion to pass through the window portion, wherein
   the adapter is prepared by using an adapter forming material containing a cycloolefin-based resin as a main component;
   wherein the (co)polymer having a structural unit derived from an α-olefin as the additive is a styrene-ethylene/butylene-styrene block copolymer; and
   wherein the (co)polymer having a structural unit derived from an α-olefin as the additive is a styrene-ethylene/butylene-styrene block copolymer.

9. The gas measurement adapter according to claim 8, wherein a styrene content in the styrene-ethylene/butylene-styrene block copolymer is 5 mass % to 60 mass %.

* * * * *